United States Patent
Swartz et al.

(10) Patent No.: US 7,153,301 B2
(45) Date of Patent: *Dec. 26, 2006

(54) PROCESS AND DEVICE FOR THE TREATMENT OF ATRIAL ARRHYTHMIA

(75) Inventors: John F. Swartz, Afton, OK (US); Michael C. Bednarek, Buffalo, MN (US); Richard E. Stehr, Stillwater, MN (US); Michael J. Coyle, Minneapolis, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/323,340

(22) Filed: Dec. 16, 2002

(65) Prior Publication Data

US 2003/0088246 A1    May 8, 2003

Related U.S. Application Data

(60) Continuation of application No. 09/859,078, filed on May 16, 2001, now Pat. No. 6,503,247, which is a division of application No. 09/281,727, filed on Mar. 30, 1999, now Pat. No. 6,235,025, which is a division of application No. 08/883,668, filed on Jun. 27, 1997, now Pat. No. 5,938,660.

(51) Int. Cl.
*A61B 18/18* (2006.01)
*A61M 29/00* (2006.01)

(52) U.S. Cl. ............... 606/41; 606/49; 604/101.01

(58) Field of Classification Search ........ 606/13–16, 606/41, 49–50; 607/98, 99, 101, 102, 122; 604/113, 101.01, 101.05
See application file for complete search history.

(56) References Cited

U.S. PATENT DOCUMENTS

| | | |
|---|---|---|
| 3,867,945 A | 2/1975 | Long |
| 4,033,331 A | 7/1977 | Guss et al. |
| 4,117,836 A | 10/1978 | Erikson |
| 4,244,362 A | 1/1981 | Anderson |
| 4,445,892 A | 5/1984 | Hussein et al. ............. 604/101 |
| 4,500,529 A | 2/1985 | Shanklin, Jr. et al. |
| 4,558,155 A | 12/1985 | Shanklin, Jr. et al. |
| 4,569,347 A | 2/1986 | Frisbie |
| 4,581,017 A | 4/1986 | Sahota |
| 4,641,649 A | 2/1987 | Walinsky et al. |
| 4,705,517 A | 11/1987 | DiPisa, Jr. |

(Continued)

FOREIGN PATENT DOCUMENTS

DE    40 01 086    7/1991

(Continued)

OTHER PUBLICATIONS

Heinz, G. et al., "Improvement in Left Ventricular Systolic Function After Successful Radiofrequency His Bundle Ablation for Drug Refractory, Chronic Atrial Fibrillation and Recurrent Atrial Flutter", Am. J. Cardiol., vol. 69, pp. 489-492 (1992).

(Continued)

*Primary Examiner*—Roy D. Gibson
(74) *Attorney, Agent, or Firm*—Heimbecher & Assoc., LLC

(57) ABSTRACT

A process for the treatment of atrial arrhythmia by use of ablation procedures comprising circumferential ablation of vessels, particularly pulmonary veins associated with the left atrium of the heart. Also disclosed are medical devices used for formation of the circumferential ablation lesions in vessels associated with the heart.

13 Claims, 11 Drawing Sheets

U.S. PATENT DOCUMENTS

| | | | |
|---|---|---|---|
| 4,721,117 A | 1/1988 | Mar et al. | |
| 4,729,384 A | 3/1988 | Bazenet | |
| 4,790,331 A | 12/1988 | Okada et al. | |
| 4,810,244 A | 3/1989 | Allen | |
| 4,838,879 A | 6/1989 | Tanabe et al. | |
| 4,867,174 A | 9/1989 | Skribiski | |
| 4,882,777 A | 11/1989 | Narula | |
| 4,883,058 A | 11/1989 | Ruiz | |
| 4,898,591 A | 2/1990 | Jang et al. | |
| 4,911,163 A | 3/1990 | Fina | |
| 4,917,102 A | 4/1990 | Miller et al. | |
| 4,935,017 A | 6/1990 | Sylvanowicz | |
| 4,945,912 A | 8/1990 | Langberg | |
| 4,955,377 A | 9/1990 | Lennox et al. | |
| 4,969,875 A | 11/1990 | Ichikawa | |
| 4,988,698 A | 1/1991 | Kato et al. | |
| 5,002,532 A | 3/1991 | Gaiser et al. | |
| 5,016,640 A | 5/1991 | Ruiz | |
| 5,100,388 A | 3/1992 | Behl et al. | 604/113 |
| 5,103,804 A | 4/1992 | Abele et al. | 128/4 |
| 5,106,360 A | 4/1992 | Ishiwara et al. | 600/2 |
| 5,120,323 A | 6/1992 | Shockey et al. | |
| 5,147,315 A | 9/1992 | Weber | |
| 5,162,911 A | 11/1992 | Burrage | |
| 5,171,232 A | 12/1992 | Castillo et al. | |
| 5,172,699 A | 12/1992 | Svenson et al. | |
| 5,209,229 A | 5/1993 | Gilli | |
| 5,215,540 A | 6/1993 | Anderhub | |
| 5,215,989 A | 6/1993 | Baldwin et al. | |
| 5,222,501 A | 6/1993 | Ideker et al. | |
| 5,228,442 A | 7/1993 | Imran | |
| 5,231,994 A | 8/1993 | Harmjanz | |
| 5,231,995 A | 8/1993 | Desai | |
| 5,242,441 A | 9/1993 | Avitall | |
| 5,246,007 A | 9/1993 | Frisbie et al. | |
| 5,246,438 A | 9/1993 | Langberg | |
| 5,256,141 A | 10/1993 | Gencheff et al. | |
| 5,263,493 A | 11/1993 | Avitall | |
| 5,267,982 A | 12/1993 | Sylvanowicz | |
| 5,271,392 A | 12/1993 | Ferek-Petric | |
| 5,279,546 A | 1/1994 | Mische et al. | |
| 5,281,213 A | 1/1994 | Milder et al. | |
| 5,281,217 A | 1/1994 | Edwards et al. | |
| 5,281,218 A | 1/1994 | Imran | |
| 5,282,836 A | 2/1994 | Kreyenhagen et al. | |
| 5,286,866 A | 2/1994 | Carr et al. | |
| 5,287,858 A | 2/1994 | Hammerslag et al. | |
| 5,290,229 A | 3/1994 | Paskar | |
| 5,293,868 A | 3/1994 | Nardella | |
| 5,295,493 A | 3/1994 | Radisch, Jr. | |
| 5,299,574 A | 4/1994 | Bower | |
| 5,304,131 A | 4/1994 | Paskar | |
| 5,304,214 A | 4/1994 | DeFord et al. | 607/105 |
| 5,312,355 A | 5/1994 | Lee | |
| 5,322,509 A | 6/1994 | Rickerd | |
| 5,366,490 A | 11/1994 | Edwards et al. | |
| 5,427,119 A | 6/1995 | Swartz et al. | |
| 5,433,729 A | 7/1995 | Adams et al. | 607/5 |
| 5,450,846 A | 9/1995 | Goldreyer | |
| 5,462,529 A | 10/1995 | Simpson et al. | |
| 5,468,239 A | 11/1995 | Tanner et al. | |
| 5,472,441 A | 12/1995 | Edwards et al. | |
| 5,476,495 A | 12/1995 | Kordis et al. | |
| 5,482,037 A * | 1/1996 | Borghi | 600/381 |
| 5,484,412 A | 1/1996 | Pierpont | |
| 5,497,774 A | 3/1996 | Swartz et al. | |
| 5,500,012 A * | 3/1996 | Brucker et al. | 607/122 |
| 5,536,247 A | 7/1996 | Thornton | 604/49 |
| 5,540,679 A | 7/1996 | Fram et al. | |
| 5,564,440 A | 10/1996 | Swartz et al. | |
| 5,575,766 A | 11/1996 | Swartz et al. | |
| 5,584,872 A | 12/1996 | LaFontaine et al. | |
| 5,588,961 A | 12/1996 | Leone et al. | |
| 5,599,307 A | 2/1997 | Bacher et al. | |
| 5,624,439 A | 4/1997 | Edwards et al. | |
| 5,628,316 A | 5/1997 | Swartz et al. | |
| 5,640,955 A | 6/1997 | Ockuly et al. | |
| 5,676,693 A | 10/1997 | LaFontaine | |
| 5,681,308 A | 10/1997 | Edwards et al. | |
| 5,722,400 A | 3/1998 | Ockuly et al. | |
| 5,746,495 A | 5/1998 | Klamm | |
| 5,785,706 A | 7/1998 | Bednarek | |
| 5,792,105 A | 8/1998 | Lin et al. | |
| 5,797,905 A | 8/1998 | Fleischman et al. | |
| 5,800,482 A | 9/1998 | Pomeranz et al. | |
| 5,807,306 A | 9/1998 | Shapland et al. | |
| 5,814,029 A | 9/1998 | Hassett | |
| 5,938,660 A | 8/1999 | Swartz et al. | |
| 5,971,983 A | 10/1999 | Lesh | |
| 6,068,629 A | 5/2000 | Haissaguerre et al. | |
| 6,097,976 A | 8/2000 | Yang et al. | |
| 6,120,500 A | 9/2000 | Bednarek et al. | |
| 6,156,018 A | 12/2000 | Hassett | |
| 6,179,824 B1 * | 1/2001 | Eggers et al. | 604/500 |
| 6,217,576 B1 | 4/2001 | Tu et al. | |
| 6,235,025 B1 | 5/2001 | Swartz et al. | |
| 6,251,109 B1 | 6/2001 | Hassett et al. | |
| 6,503,247 B1 | 1/2003 | Swartz et al. | |
| 6,526,302 B1 | 2/2003 | Hassett | |
| 6,540,744 B1 | 4/2003 | Hassett et al. | |

FOREIGN PATENT DOCUMENTS

| | | |
|---|---|---|
| EP | A 656217 | 6/1995 |
| EP | A 670168 | 9/1995 |
| WO | WO 92/12754 | 8/1992 |
| WO | WO 92/19307 | 11/1992 |
| WO | WO 96/00042 | 1/1996 |
| WO | WO 97/16127 | 5/1997 |

OTHER PUBLICATIONS

Huang, S. K. et al., "Closed Chest Catheter Desiccation of the Atrioventricular Junction Using Radiofrequency Energy—A New Method of Catheter Ablation", J. Am. Coll. Cardiol., vol. 9, pp. 349-358 (1987).

Gallagher, J. J. et al., Catheter Technique for Closed-Chest Ablation of the Atrioventricular Conduction System, N. Engl. J. Med., vol. 306, pp. 194-200 (1982).

Saul, J. P. et al., "Catheter Ablation of Accessory Atrioventricular Pathways in Young Patients: Use of Long Vascular Sheaths, the Transseptal Approach and a Retrograde Left Posterior Parallel Approach", J. Amer. Coll. Card., vol. 21, No. 3, pp. 571-583 (Mar. 1, 1993).

Scheinman, M. M. et al., "Catheter-Induced Ablation of the Atrial Ventricular Juncture to Control Rafractory Supraventricular Arrhythmias", JAMA, vol. 248, pp. 851-855 (1982).

Swartz, J. F. et al., "Radiofrequency Endocardial Catheter Ablation of Accessory Atrioventricular Pathway Atrial Insertion Sites", Circulation, vol. 87, No. 2, pp. 487-499 (Feb. 1993).

Tracey, C. N., "Radiofrequency Catheter Ablation of Ectopic Atrial Tachycardia Using Paced Activation Sequence Mapping", J. Am. Coll. Cardiol., vol. 21, pp. 910-917 (1993).

Cox, J. L. et al., Electrophysiology, Pacing and Arrhythmia, "Operations for Atrial Fibrillation", Clin. Cardiol. vol. 14, pp. 827-834 (1991).

Cox, J. L. et al., "The Surgical Treatment of Atrial Fibrillation", The Journal of Thoracic and Cardiovascular Surgery, vol. 101, No. 4, pp. 569-592 (Apr. 1991).

Cox, J. L. et al., "The Surgical Treatment of Atrial Fibrillation", The Journal of Thoracic and Cardiovascular Surgery, vol. 101, No. 4, pp. 406-426 (Mar. 1991).

Falk, R. H. et al., Atrial Fibrillation Mechanisms and Management, pp. 359-374 (1992).

Horowitz, L. N., Current Management of Arrhythmias, pp. 373-378 (1991).

Martin, D. et al., "Artial Fibrillation", pp. 35-41 (1994).

Martin, D. et al., "Atrial Fibrillation", pp. 42-59 (1994).

Martin, D. et al., "Atrial Fibrillation", pp. 52-59 91994).

Singer, I. et al., "Catheter Ablation of Arrhythmias", Clinical Manual of Electrophysiology, pp. 421-431 (1993).

Haissaguerre, M. et al., "Right and Left Atrial Radiofrequency Catheter Therapy of Paroxysmal Atrial Fibrillation", Journal of Cardiovascular Electrophysiology, vol. 7, No. 12, pp. 1132-1144 (Dec. 1996).

* cited by examiner

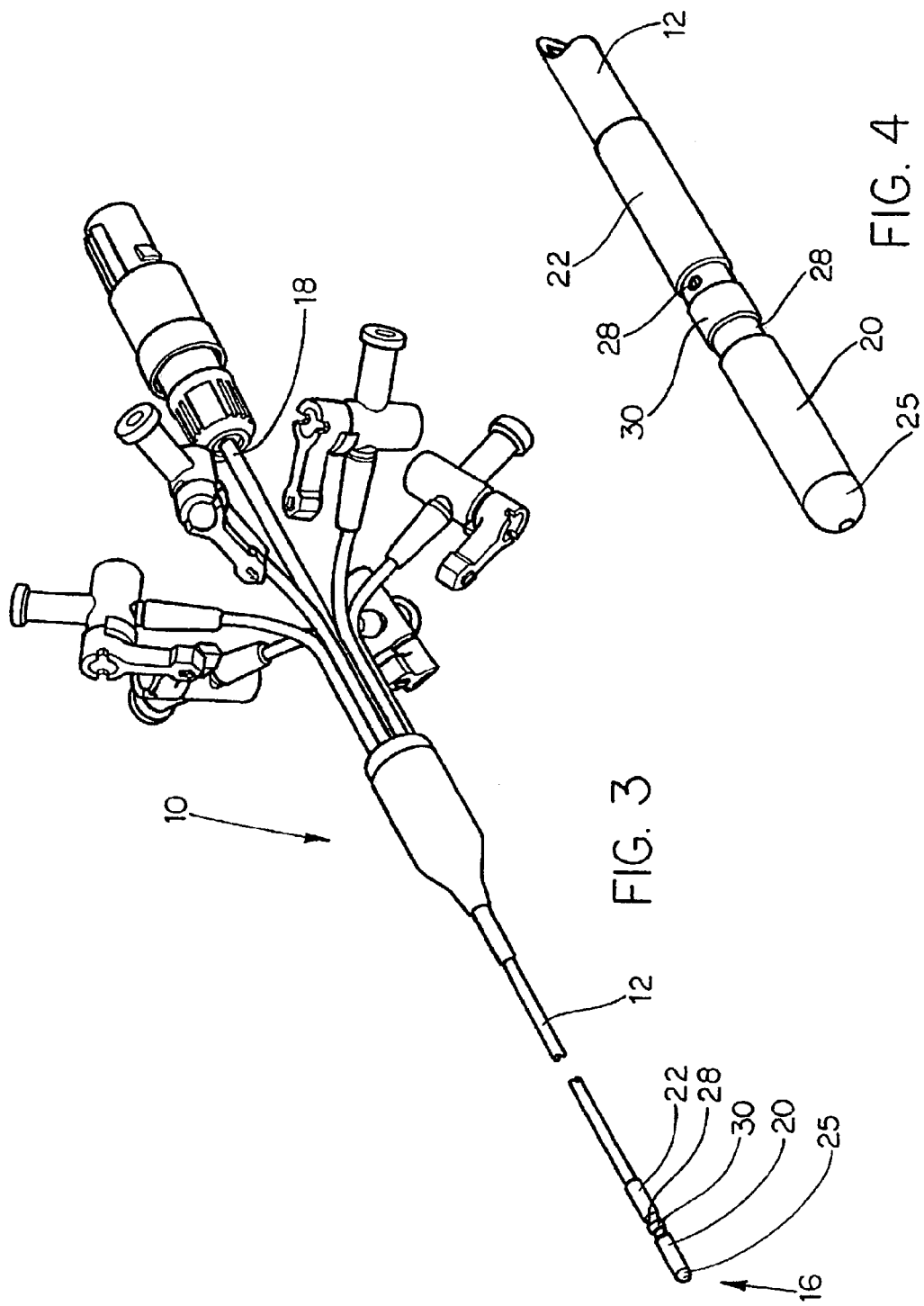

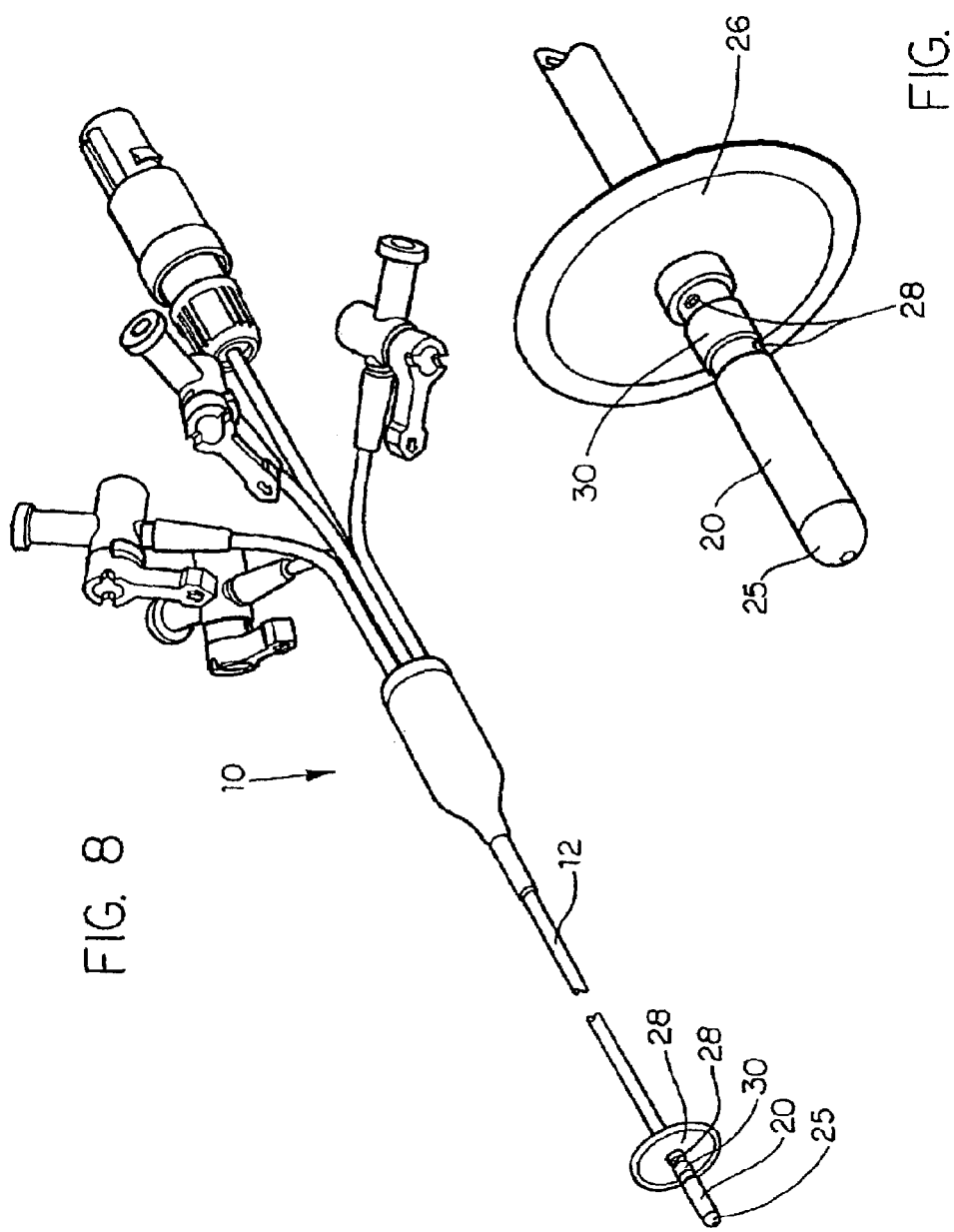

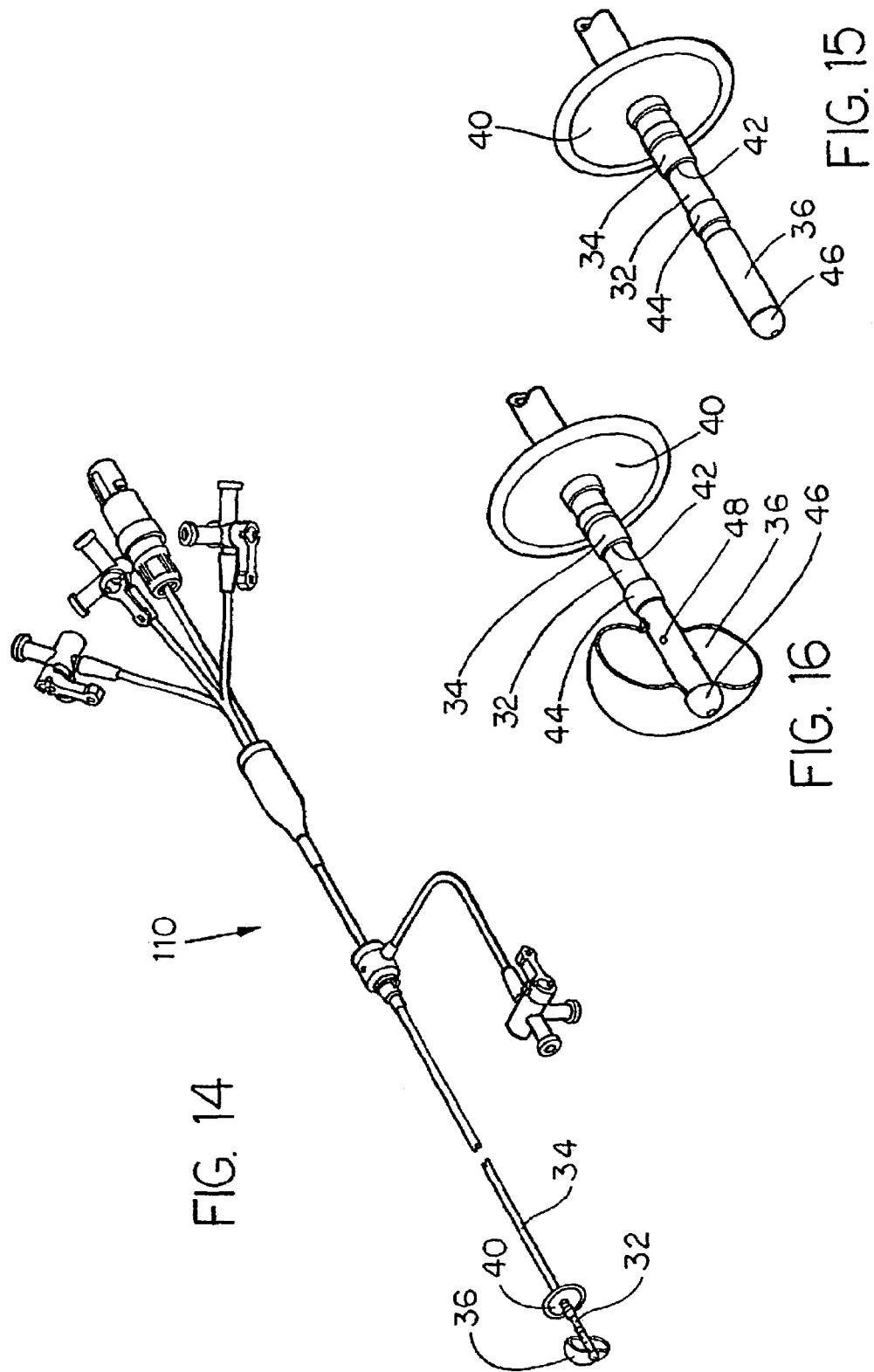

PROCESS AND DEVICE FOR THE TREATMENT OF ATRIAL ARRHYTHMIA

CROSS-REFERENCE TO RELATED APPLICATIONS

This application is continuation of U.S. application Ser. No. 09/859,078, filed May 16, 2001 now U.S. Pat. No. 6,503,247, allowed, which is a division of U.S. application Ser. No. 09/281,727, filed on Mar. 30, 1999, now U.S. Pat. No. 6,235,025, which is a division of U.S. application Ser. No. 08/883,668, filed on 27 Jun. 1997, now U.S. Pat. No. 5,938,660.

BACKGROUND OF INVENTION

This invention relates to medical devices and processes useful for the treatment of atrial arrhythmia. In particular, it relates to a preferred process and medical device used for ablation procedures in vessels of the human body. Introducers and catheters have been in use for medical procedures for many years. For example, one procedure utilizes a catheter to convey an electrical stimulus to a selected location within the human body. Another procedure utilizes a catheter to monitor locations in the body for diagnostic tests. Catheters may examine, diagnose and treat while positioned at a specific location within the body which is otherwise inaccessible without more invasive procedures. In use, catheters may be inserted into a major vein or artery which is near the body surface. These catheters are then guided to a specific location for examination, diagnosis and treatment by manipulating the catheter through the artery or vein of the human body, frequently with the assistance of other medical devices, such as introducers or guidewires.

One common medical procedure utilizing specialized catheters is the treatment of vessels located within the human body, frequently vessels associated with the human heart. Those procedures, most notably angioplasty procedures, utilize a catheter which often contains an inflatable balloon secured to the catheter. In some of these medical procedures, the catheter contains a pair of inflatable balloons used to limit the portion of the vessel that is treated and/or to assure that the catheter remains at a fixed location within the vessel throughout the medical procedure.

Multiple balloon catheters are utilized throughout the body. For example, U.S. Pat. No. 5,468,239 discloses a device for circumferential laser burning of tissue in a urethral canal. This device utilizes a pair of cuffs or balloons (60) with a laser probe (12) located between those balloons. U.S. Pat. No. 5,588,961 discloses an infusion catheter for delivery of medication to a vessel and contains a pair of balloons (16, 17) and an electrode (35) secured to the catheter. Ports are provided in the catheter to introduce the medication into the space between the two balloons within the vessel. EMF energy may also be introduced into the electrode to encourage the movement of the medication away from the catheter toward the walls of the vessel. U.S. Pat. No. 5,256,141 discloses a pair of balloons (14, 18) with an electrode secured to a catheter to apply a controlled electric charge to material introduced into the space in the vessel between the two balloons. Biological material is introduced into this space for medical treatment of the vessel. U.S. Pat. No. 5,366,490 discloses a pair of balloons (30, 32) secured to a catheter and a stylette (36) through which radio frequency energy is supplied to destroy tissue. U.S. Pat. No. 5,599,307 discloses a pair of balloons (41, 42) secured to a catheter designed to occlude a vessel. Finally, U.S. Pat. No. 5,002,532 discloses a pair of balloons (21, 22) secured to a catheter (12) for use in a dilation procedure within a vessel, whereby the two balloons may be inflated to different levels.

In addition to the use of multiple balloons on a single catheter for medical procedures, U.S. Pat. No. 5,462,529 discloses a medical device containing a pair of catheters (12, 28), each containing a balloon (20, 48) secured at or near its distal end, which device is utilized to perform a medical procedure within a vessel. U.S. Pat. No. 5,484,412 also discloses a pair of catheters (18, 22) utilized to perform a medical procedure within a vessel, each containing an inflatable balloon (36, 38). U.S. Pat. No. 4,911,163 discloses a pair of balloons (2, 8) secured to a pair of catheters (1, 7) for introduction of medicine or diagnostic fluids into the space between the two balloons.

Atrial fibrillation is the most common sustained heart arrhythmia. It is estimated to occur in upwards of 0.4 percent of the adult population and perhaps as many as 10 percent of the population who are 60 years or older. Cox, J. L., et al., Electrophysiology, Pacing and Arrhythmia, "Operations for Atrial Fibrillation," Clin. Cardiol. 14, 827–834 (1991). Atrial arrhythmia may be transient or persistent. While most atrial arrhythmia occurs in individuals having other forms of underlying heart disease, some atrial arrhythmias occur independently. While atrial arrhythmias do not directly cause death as frequently as ventricular arrhythmias, they increase the risk factors for a number of other diseases such as systemic and cerebral embolism and may cause a number of additional medical problems.

In the treatment of atrial fibrillation, antiarrhythmic drugs sometimes provide relief. Anti-arrhythmia drugs are disclosed, for example, in U.S. Pat. Nos. 4,558,155, 4,500,529, 4,988,698, 5,286,866 and 5,215,989. The treatment of atrial arrhythmia by pharmaceutical has been disclosed in a number of medical articles and books including, for example, Martin, D., et al., Atrial Fibrillation, pgs. 35–41 (1994); Falk, R. H., et al., Atrial Fibrillation (1992); Singer, I., et al., Clinical Manual of Electrophysiology (1993); and Horowitz, L. N., Current Management of Arrhythmias (1991).

Another treatment for atrial arrhythmia or fibrillation involves the use of an implanted atrial defibrillator or cardioversion. See, for example, U.S. Pat. Nos. 5,282,836, 5,271,392 and 5,209,229 and Martin, D., et al., Atrial Fibrillation, pgs. 42–59 (1994).

Certain patients with symptomatic or life threatening atrial arrhythmias, however, cannot be adequately treated by drugs or these medical devices. Other forms of aggressive treatment are mandated, which have in the past often included surgery. For example, a surgical procedure for the treatment of atrial arrhythmia known as the "Maze" procedure is discussed in Cox, J. L. et al., Electrophysiology, Pacing and Arrhythmia, "Operations for Atrial Fibrillation," Clin. Cardiol. Vol. 14, pgs. 827–834 (1991). See also Cox, J. L., et al., "The Surgical Treatment of Atrial Fibrillation," The Journal of Thoracic and Cardiovascular Surgery, Vol. 101, No. 4, pgs. 569–592 (April, 1991), and Cox, J. L., et al., "The Surgical Treatment of Atrial Fibrillation," The Journal of Thoracic and Cardiovascular Surgery, Vol. 101, No. 4, pgs. 406–426 (March, 1991). Other surgical procedures for atrial arrhythmia are discussed, for example, in Martin, D., et al., Atrial Fibrillation, pgs. 54–56 (1994).

Another procedure increasingly used within the last 10 to 15 years for the treatment of certain types of cardiac arrhythmia involves ablation of cardiac tissue. For example, this procedure has been used to interrupt or modify existing conduction pathways associated with arrhythmias within the heart. The particular area for ablation depends on the type of underlying arrhythmia. The use of radio frequency catheter ablation for the treatment of paroxysmal atrial fibrillation is disclosed in Haissaguerre, M., et al., "Right and Left Atrial Radiofrequency Catheter Therapy of Paroxysmal Atrial Fibrillation" *J. Cardiovascular Electrophysiology*, V.7, pgs. 1132–1144 (December 1996). Ablation procedures are also used for the treatment of atrioventricular (AV) nodal reentrant tachycardia. With this condition, ablation of the fast or slow AV nodal pathways has become an accepted treatment. Singer, I., et al., "Catheter Ablation for Arrhythmias" *Clinical Manual of Electrophysiology*, pgs. 421–431 (1993); Falk, R. H., et al., *Atrial Fibrillation Mechanisms in Management*, pgs. 359–374 (1992); Horowitz, L. N., *Current Management of Arrhythmias*, pgs. 373–378 (1991); and Martin, D., et al., *Atrial Fibrillation*, pgs. 42–59 (1994). In addition, the use of ablation catheters for ablating locations within the heart has been disclosed, for example in U.S. Pat. Nos. 4,641,649, 5,263,493, 5,231,995, 5,228,442 and 5,281,217.

The sources of energy used for catheter ablation vary. Initially, high voltage, direct current (DC) ablation techniques were commonly used. However, because of problems associated with the use of DC current, radio frequency (RF) energy has become the preferred source of energy for ablation procedures. The use of RF energy for ablation has been disclosed, for example, in U.S. Pat. Nos. 4,945,912, 5,209,229, 5,281,218, 5,242,441, 5,246,438, 5,281,213 and 5,293,868. Other energy sources which are being used currently or are being considered for ablation of heart tissue include laser, ultrasound, microwave and fulgutronization.

Ablation of a precise location within the heart requires the precise placement of the ablation catheter within the heart. Precise positioning of the ablation catheter is especially difficult because of the physiology of the heart, particularly as the ablation procedures generally occur while the heart is beating. Commonly, the placement of the catheter is determined by a combination of electrophysiological guidance and fluoroscopy (placement of the catheter in relation to known features of the heart which are marked by radiopaque diagnostic catheters which are placed in or at known anatomical structures such as the coronary sinus, high right atrium and the right ventricle).

A process for the mapping and treatment of atrial arrhythmia using ablation catheters guided to a specific location by shaped, guiding introducers is disclosed in U.S. Pat. Nos. 5,427,119, 5,497,774, 5,575,766, 5,564,440, 5,628,316 and 5,640,955. In particular, a process for the ablation of defined tracks within the left and/or right atrium as an element of the treatment of atrial fibrillation is disclosed in U.S. Pat. No. 5,575,766.

The mechanism for initiation of some forms of atrial arrhythmia, such as atrial premature contractions, is not well understood. As a result, ablation procedures up to the present have focused on the formation of lesions within the chambers of the heart at selected locations which will either prevent the passage of electrical signals associated with atrial premature contractions or prevent the formation of improper electrical pathways within the heart which can result in atrial arrhythmia.

It has been surprisingly discovered that one source for these atrial premature contractions originates deep within vessels associated with the heart, in particular the pulmonary veins. Once these atrial premature contractions form in the pulmonary veins, they are periodically conducted into the left atrium. When the atrial premature contractions enter the left atrium, they can initiate or continue an episode of atrial fibrillation.

Invasive treatment of atrial fibrillation in the past has been limited to the formation of lesions around the pulmonary veins in the left atrium created by an invasive surgical procedure, such as is disclosed by Cox, J. L., et al., Electrophysiology, Pacing and Arrhythmia, "Operations for Atrial Fibrillation" *Clin. Cardiol.* Vol. 14, pgs. 827–834 (1991). In addition, the use of precurved guiding introducers to guide ablation catheters to appropriate locations in the left atrium for use in the formation of lesions around the pulmonary veins has been disclosed in U.S. Pat. No. 5,575,766.

While these procedures have been successful in some patients, other patients require additional treatment or the treatments previously proposed have not been completely successful in the elimination of the atrial fibrillation. In addition, these ablation procedures are very time consuming, requiring as long as 10–15 hours.

It is therefore an aspect of this invention to disclose a medical device useful in the treatment of atrial arrhythmia, particularly atrial fibrillation.

It is an additional aspect of this invention to disclose a medical device useful for the formation of circumferential ablation lesions in vessels in the body.

It is a still further aspect of this invention to disclose a medical device containing a pair of inflatable balloons and an RF energy ablation electrode, which device is utilized to form a circumferential ablation lesion for the treatment of atrial arrhythmia, particularly atrial premature contractions.

It is a still further aspect of this invention to disclose a medical device for the chemical ablation of tissue within a vessel.

It is a still further aspect of this invention to disclose a process for the formation of ablation lesions in vessels in the human body.

It is a still further aspect of this invention to disclose a process for ablation within the pulmonary veins.

It is a still further aspect of this invention to disclose a process for the formation of circumferential lesions in vessels.

It is a still further aspect of this invention to disclose medical procedures for the production of circumferential ablation lesions within vessels of the heart for the treatment of atrial fibrillation.

It is a still further aspect of this invention to disclose a process for the formation of ablation lesions within a vessel using RF energy.

It is a still further aspect of this invention to disclose a process for the formation of ablation lesions within a vessel using chemical ablative agents.

These and other aspects can be obtained by the disclosed processes for the treatment of atrial arrhythmia and the design of the medical products for use with those processes which are disclosed by the instant invention.

SUMMARY OF INVENTION

The present invention is a medical device for ablation within a vessel of a human and includes a catheter. A first seal is secured to the catheter to seal the vessel and prevent substantially the flow of blood through the vessel. A second seal is secured to the catheter located proximal from the first seal, to limit the backflow of blood into the vessel. An introducing system is also secured to the catheter to introduce a conductive media into the vessel at a location in communication with the first and second seals. An ablating system is secured to the catheter for ablating tissue within the vessel. The ablating system is located between the first and second seals.

The seals preferably are either inflatable balloons or flexible disks attached to the catheter. The ablating system preferably is an RF energy ablation electrode.

Alternatively, the present invention is a medical system for ablation within a vessel of a human and includes an introducer with a proximal and distal end and a lumen passing from its proximal to its distal end. A catheter is inserted within the lumen of the introducer. A first seal is secured to the catheter to seal the vessel and prevent substantially the flow of blood through the vessel. A second seal is secured to the introducer at or near its distal end to substantially limit the backflow of blood into the vessel. An introducing system to introduce conductive media into the vessel at a location is in communication with the first and second seal members. An ablating system for ablating tissue within the vessel is located between the first and second seals.

Also disclosed is a process for the ablation of tissue within a vessel of a human which includes introducing a catheter containing a first seal into the vessel, sealing the vessel to prevent substantially the flow of blood through the vessel using the first seal, substantially sealing a location within the vessel proximal to that sealed by the first seal to substantially limit the backflow of blood into the vessel by use of a second seal, placing an ablating system for ablating the tissue associated with the vessel at a location in the vessel between the first and second seals, substantially replacing blood present in a space in the vessel between the first and second seals with a conductive media, and while substantially preventing blood from entering the space between the first and second seals, forming an ablation lesion in the tissue of the vessel located between the first and second seals by use of the ablating system.

An alternative preferred process for ablation of tissue within a vessel associated with a human includes introducing an introducer into the vessel, where the introducer contains a lumen passing from its proximal to its distal end, introducing within the lumen of the introducer a catheter, where there is secured at or near a distal end of the catheter a first seal and an ablating system, and where there is secured at or near the distal end of the introducer a second seal, advancing the catheter within the lumen of the introducer, where the first seal and the ablation system extend beyond the distal tip of the introducer, substantially preventing the flow of blood through the vessel at a first location within the vessel by use of the first seal, substantially sealing a second location within the vessel proximal to the first location by the second seal to substantially limit the backflow of blood into the vessel, substantially removing blood located in the vessel from a space between the first and second seals by introduction of a conductive media into that space, and while substantially preventing additional blood from being introduced into the space between the first and second seals, ablating tissue of the vessel between the first and second seals by the ablating system.

The instant invention also includes specific components for each of the medical devices which are used in the processes for ablation of tissue within the vessel.

BRIEF DESCRIPTION OF THE DRAWINGS

FIG. 3 is a perspective view of the first embodiment of the ablation catheter of the present invention with two balloons which are secured to the catheter not inflated.

FIG. 4 is a perspective view of a distal portion of the ablation catheter of FIG. 3 with balloons not inflated.

FIG. 8 is a perspective view of a second embodiment of the ablation catheter of the present invention utilizing a disk and a single, not inflated balloon.

FIG. 9 is a perspective view of a distal portion of the ablation catheter of FIG. 8 with the single balloon not inflated.

FIG. 14 is a perspective view of an alternative embodiment of the medical system of FIG. 11 showing the use of a single balloon secured to the catheter and a disk secured to the introducer with the balloon inflated.

FIG. 15 is a perspective view of a distal portion of the medical system of FIG. 14 with the balloon not inflated.

FIG. 16 is a perspective view of the distal portion of the medical system of FIG. 14 with the balloon inflated.

DETAILED DESCRIPTION OF THE PREFERRED EMBODIMENT

Figure 1:
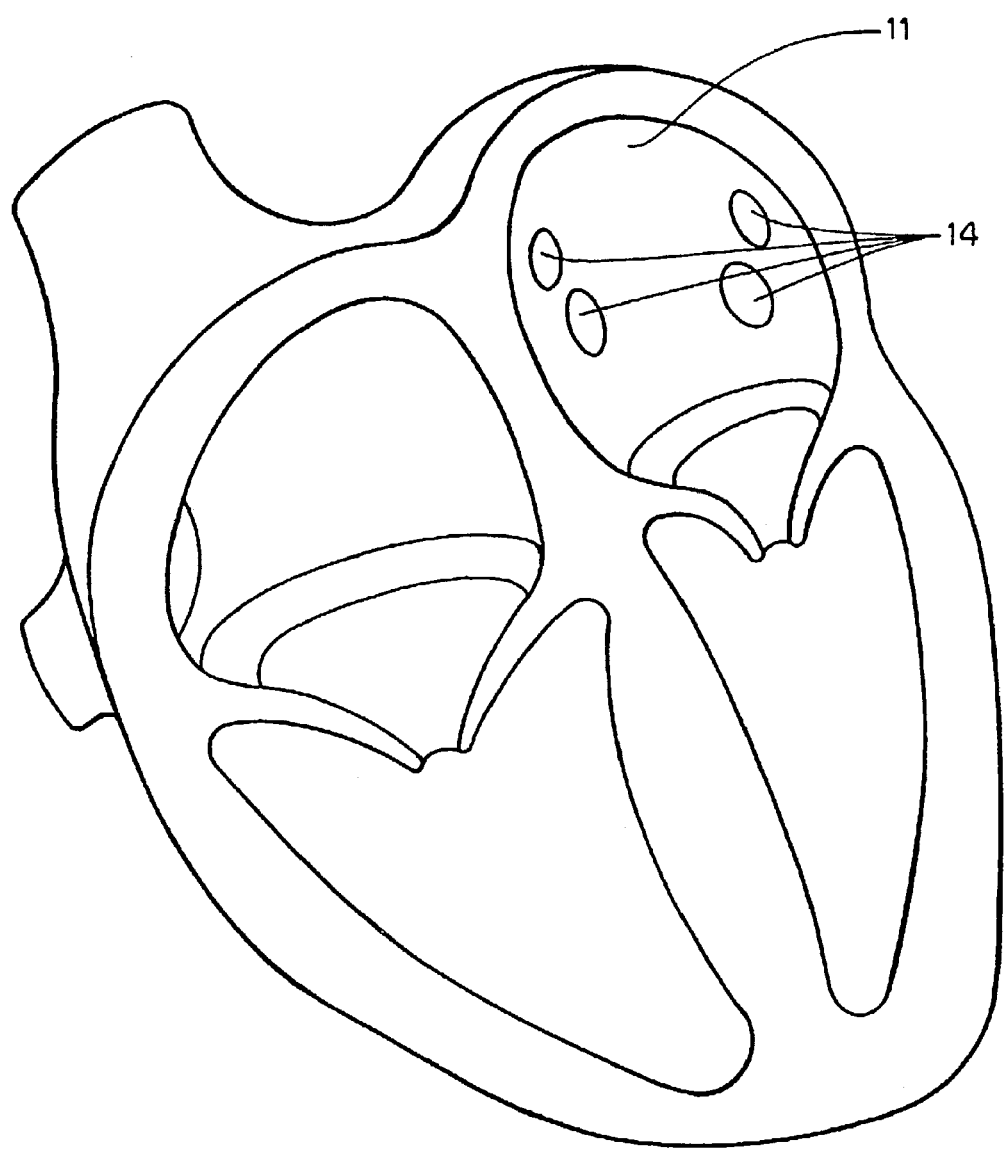
FIG. 1 is a cut away view of the heart showing the left atrium and the four pulmonary veins.

A typical human heart includes a right ventricle, a right atrium, a left ventricle and a left atrium. The right atrium is in fluid communication with the superior vena cava and the inferior vena cava. The atrioventricular septum separates the right atrium from the right ventricle. The tricuspid valve contained within the atrioventricular septum provides communication between right atrium and the right ventricle. On the inner wall of the right atrium where it is connected with the left atrium is a thin walled, recessed portion, the fossa ovalis. A drawing of the left atrium (11) and the openings (os) into the pulmonary veins (14) is shown in FIG. 1.

In the normal heart, contraction and relaxation of the heart muscle (myocardium) takes place in an organized fashion as electrochemical signals pass sequentially through the myocardium from the sinoatrial (SA) node to the atrioventricular (AV) node and then along a well defined route which includes the His-Purkinje system into the left and right ventricles. Initial electric impulses are generated at the SA node and conducted to the AV node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the atrium which are referred to as atrial arrhythmia. Three of the most common arrhythmia are ectopic atrial tachycardia, atrial fibrillation and atrial flutter. Atrial fibrillation can result in significant patient discomfort and even death because of a number of associated problems, including: (1) an irregular heart rate which causes the patient discomfort and anxiety, (2) loss of synchronous atrioventricular contractions which compromises cardiac hemodynamics resulting in varying levels of congestive heart failure, and (3) stasis of blood flow, which increases the vulnerability of the patient to thromboembolism.

Efforts to alleviate these problems in the past have included significant usage of pharmacological treatments. Occasionally surgical procedures have also been utilized in the treatment of atrial arrhythmia. Another procedure for treatment of atrial arrhythmia involves ablating the His bundle. It has been discovered that similar success can be achieved without invasive surgery by ablation procedures performed within the atria as disclosed in U.S. Pat. No. 5,575,766. To accomplish this non-invasive procedure successfully, the ablation catheter must be positioned at predetermined locations within the right and left atria to ablate predetermined tracks, thus forming a natural barrier to the formation of the reentry circuits.

The specific pathological cause for atrial fibrillation is not well understood. It has been surprisingly discovered that one source for atrial premature contractions which may cause atrial fibrillation, particularly paroxysmal atrial fibrillation, originates in the pulmonary veins associated with the left atrium of the heart.

Figure 2:
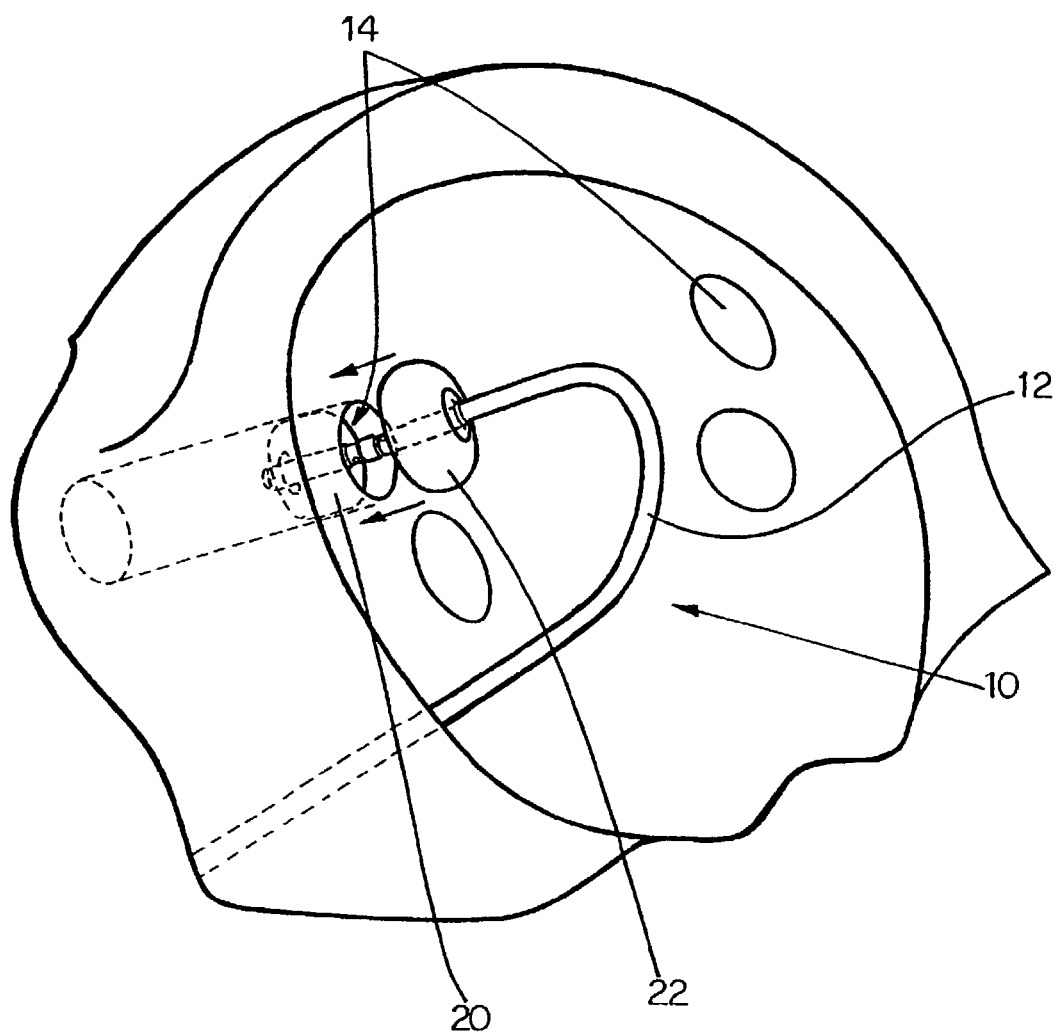
FIG. 2 is a cut away side view of the left atrium showing the first embodiment of the ablation catheter of the present invention partially introduced within one of the pulmonary veins.

In order to understand the structure of the medical devices of the invention, the medical procedure for their use within the heart must first be understood. In use, the medical device of the present invention is advanced into the left atrium and is then introduced into the appropriate pulmonary vein as shown in FIG. 2. (It is understood that ablation procedures as encompassed by the present invention may be necessary in more than one of the pulmonary veins. However, for purposes of discussion of this invention, the process will be limited to a single medical procedure performed in a single pulmonary vein.) Once in place, the ablation catheter creates a lesion which electrically isolates the source of an atrial premature contraction in the pulmonary vein from connection with the left atrium.

The pulmonary veins are generally tubular in structure, increasing in size as they open into the left atrium. It has been discovered that the conduction of atrial premature contraction through the pulmonary vein into the left atrium can be completely halted by formation of a circumferential ablation lesion around the pulmonary vein at a location proximal from the source of the atrial premature contraction. Merely ablating a single point in the pulmonary vein, which is perceived to be the source of the premature atrial contraction, may not be sufficient to isolate the source of the atrial premature contraction from the left atrium. Any medical device or system that can be used to form this circumferential ablation inside the pulmonary vein is within the context of this invention.

Because the pulmonary vein returns blood into the left atrium and because heating of blood during an ablation procedure may result in the formation of blood clots, it is critical to a successful procedure that substantially all of the blood in the pulmonary vein be removed from that area of the pulmonary vein where the ablation lesion is being formed.

It is also important that the medical practitioner be able to monitor the electrical activity of the pulmonary vein both before and after the ablation procedure to assure that the source of atrial premature contraction has been successfully isolated from the left atrium.

Conventional procedures for ablation within the heart generally utilize either a conventional tip electrode or one or more ring electrodes on an ablation catheter. To effectively ablate tissue, these electrodes are relatively small in diameter, usually in the range of about 5 French to about 8 French (1 French equals one-third millimeter (0.013 in.)). Because the diameter of a pulmonary vein may be as large as about 20 millimeters (0.79 in.), it is impractical to use a conventional ablation electrode on a conventional ablation catheter to form the circumferential lesion around the inside of a pulmonary vein.

The steps of the process in one embodiment for the formation of a circumferential ablation lesion within a pulmonary vein include introducing into a pulmonary vein a catheter or other medical device containing a seal to prevent the flow of blood through the pulmonary vein, introducing a second seal into the pulmonary vein to a location proximal from the first seal, substantially preventing the backflow of blood into the pulmonary vein from the left atrium utilizing the second seal, substantially removing blood located in a space in the pulmonary vein between the first and second seal by introducing a conductive media, introducing an ablating system for ablating tissue into that space, and while substantially preventing blood from entering that space, ablating tissue within the pulmonary vein at a location proximal to the source of the atrial premature contraction to form a circumferential lesion.

The first seal prevents blood from flowing into the area where the ablation procedure will occur. The conductive media introduced into the space between the first and second seals replaces this blood and also conducts the ablating energy, preferably radio frequency energy, to the tissue to be ablated. The second seal, which is located proximal from the first seal, prevents blood from back flowing from the left atrium into the space between the two seals. While the first seal must form a tight seal about the wall of the vessel to prevent the flow of any blood from the vessel into the space between the first and second seals, the second seal preferably is not tightly secured against the walls of the vessel, thus permitting the conductive media introduced into the space between the first and second seals to replace the blood normally present in that space. In addition, the conductive media cleans that space of any blood that may seep into the space between the two seals, conducts the energy from the ablating source to the tissue to be ablated and also flows out of the space around sides of the second seal. By evacuating blood from the space between the first and second seals and replacing it with conductive media, clots of blood are prevented from forming.

In a first preferred embodiment, the medical device (10) contains first and second seals (20, 22) as shown in FIGS. 3–10. The seals are secured to a single medical instrument, preferably a catheter (12). The catheter (12) is inserted into a pulmonary vein (14) as shown in FIG. 2. In an alternate preferred embodiment as shown in FIGS. 11–16, the first seal (36) is secured to a catheter (32) which is introduced within the lumen of an introducer (34) onto which the second seal (38) is secured. The specific structure of the mechanism of the various inventions will now be discussed in detail.

The catheter (12) of the first embodiment of the present invention contains distal and proximal ends (16, 18). The composition of the catheter (12) is conventional and should be sufficiently pliable to permit the catheter to be advanced through the vasculature into the heart and ultimately into a pulmonary vein. While the distal portion (16) of the catheter (12) may be more pliable than the remaining portions of the catheter (12), the pliability of the catheter (12) may also be consistent throughout the length of the catheter (12). An increase in pliability can be achieved through conventional procedures well known in the industry. To assist in the advancement of the catheter through the vasculature, the main portion of the catheter may be stiffer and less pliable than the distal portion. In one embodiment, this main portion can be formed of any conventional catheter material having shape memory or permitting distortion from and subsequent substantial return to its desired shape. This main portion may also be reinforced, for example, by use of a reinforcing braid or other such suitable strand material having high temporal strength. The enhanced pliability of the distal portion of the catheter can be achieved by a number of methods well known in the industry, including the use of a fused flexible tip catheter or soft tipped catheters comprised of the same or similar materials with similar performance characteristics as are present in the reinforced portion of the catheter. In addition, a more pliable distal portion of the catheter can be created through modifications made in the catheter such as by additional drawing of the catheter body to reduce the thickness of the walls thus achieving the enhanced pliability.

The overall length of the catheter should be about 50 to about 150 cm (20 to about 60 in.).

The components of the invention for use in the formation of circumferential lesions are generally secured to the catheter near or at its distal end (16). These elements include at least the following: a pair of seals (20, 22), secured at different locations on the distal portion of the catheter (12) forming a space between them, a system to introduce conductive media into the space between the first and second seals (20, 22), and an ablating system located between the first and second seals (20, 22) for ablating tissue. In addition, other elements may be secured to the catheter to assist in the formation of circumferential ablation lesions, including, for example: sensors to sense the presence of premature atrial contractions, temperature sensing for sensing the temperature of the tissue being ablated, markers for marking the location of the catheter and its components within the vessel and other conventional components normally associated with an ablation catheter.

The two seals secured to the catheter are preferably inflatable balloons (20, 22) secured to the surface of the catheter (12) as shown in FIGS. 3, 4, 5, 6 and 7. The balloons typically measure approximately 15 mm (0.59 in) in length and when inflated, generally conform to an ellipsoid shape. The maximum diameter of the balloons when fully inflated may vary from about 15 mm to about 20 mm (0.59 in. to about 0.78 in.). They are manufactured according to conventional technology from materials such as a flexible or thermoplastic rubber, urethane, latex, cellulose or other conventional materials.

Figure 5:
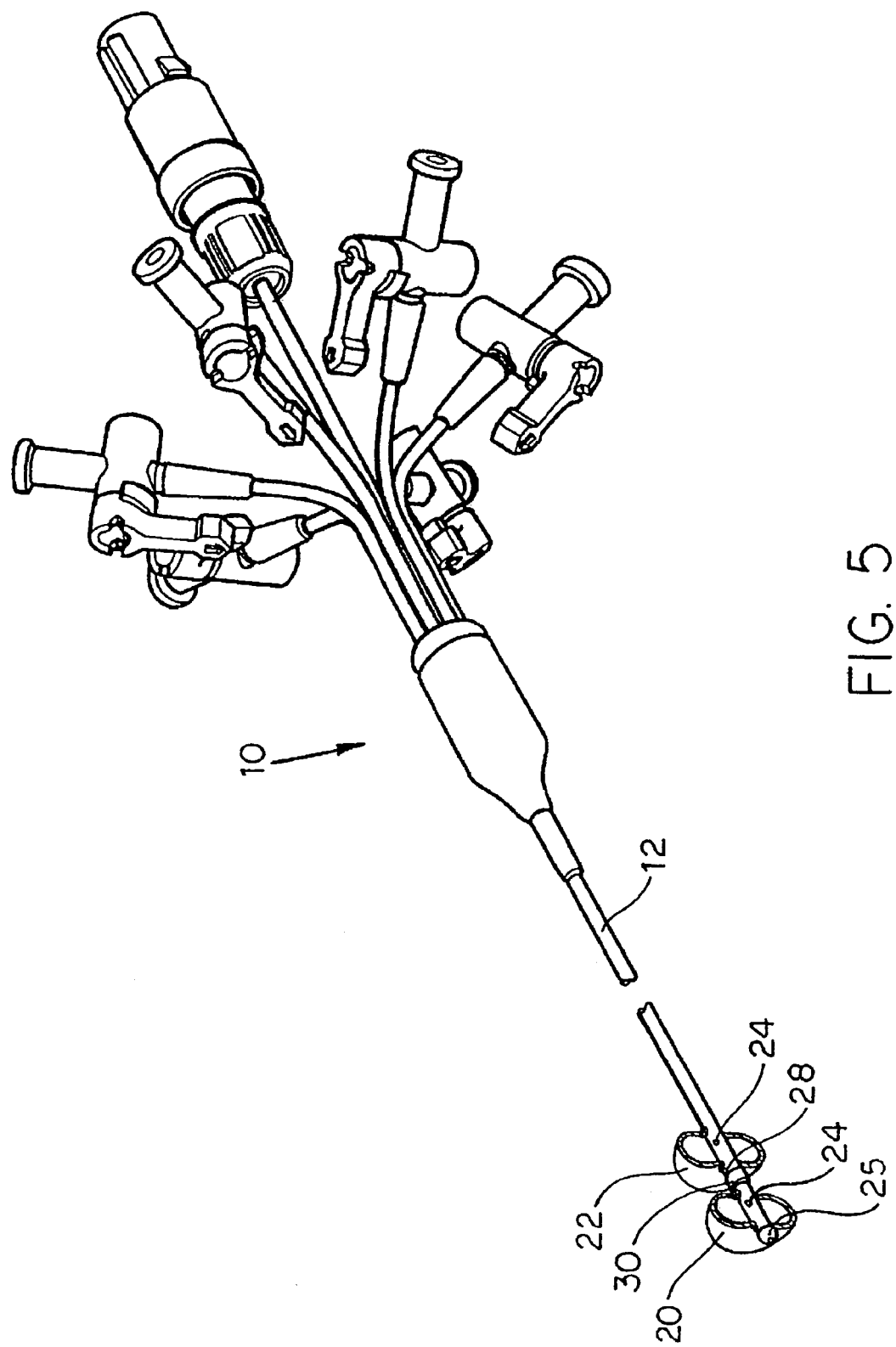
FIG. 5 is a perspective view of the first embodiment of the ablation catheter of FIG. 3 with balloons inflated.
Figure 6:
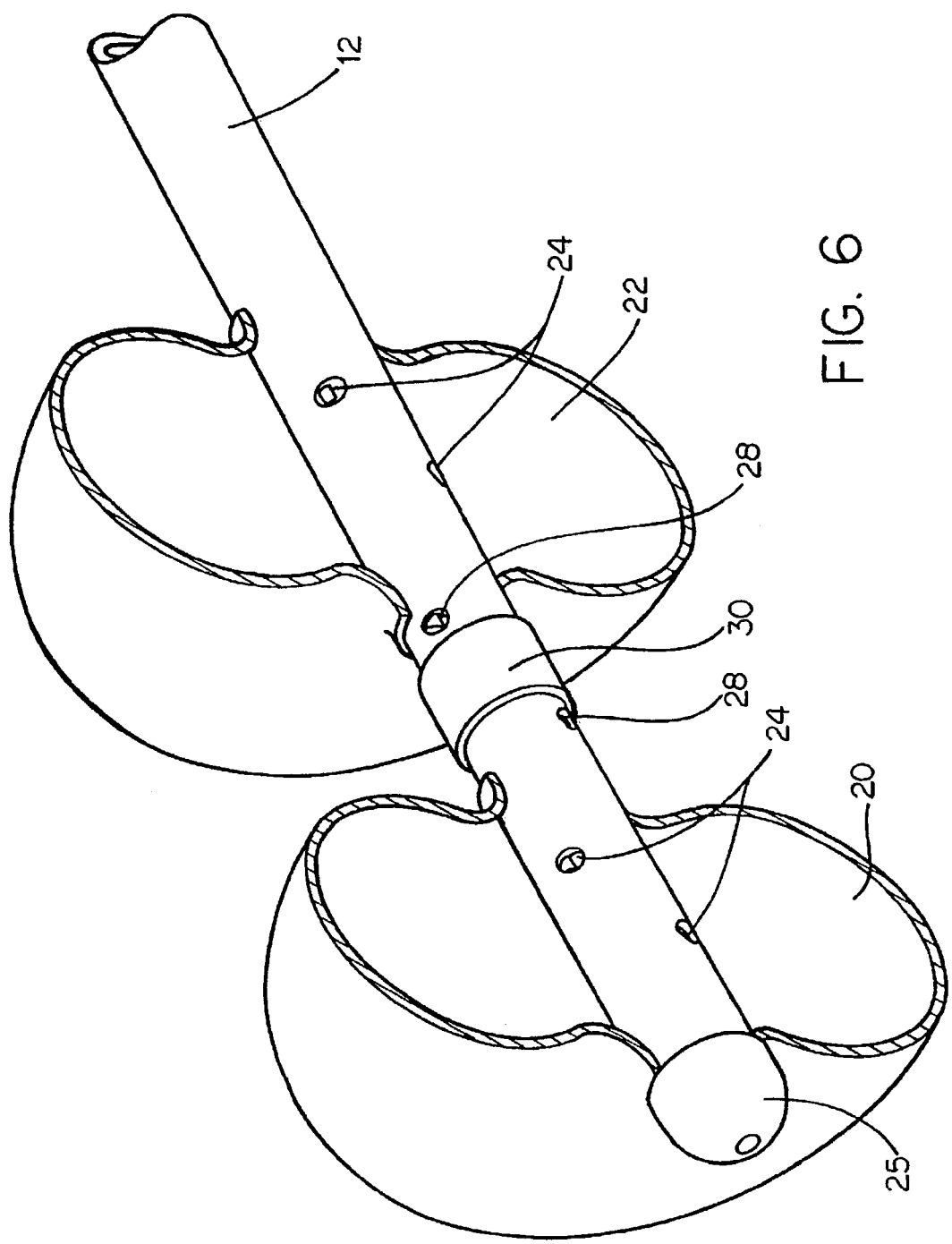
FIG. 6 is a perspective view of a distal portion of the ablation catheter of FIG. 3 with balloons inflated.
Figure 7:
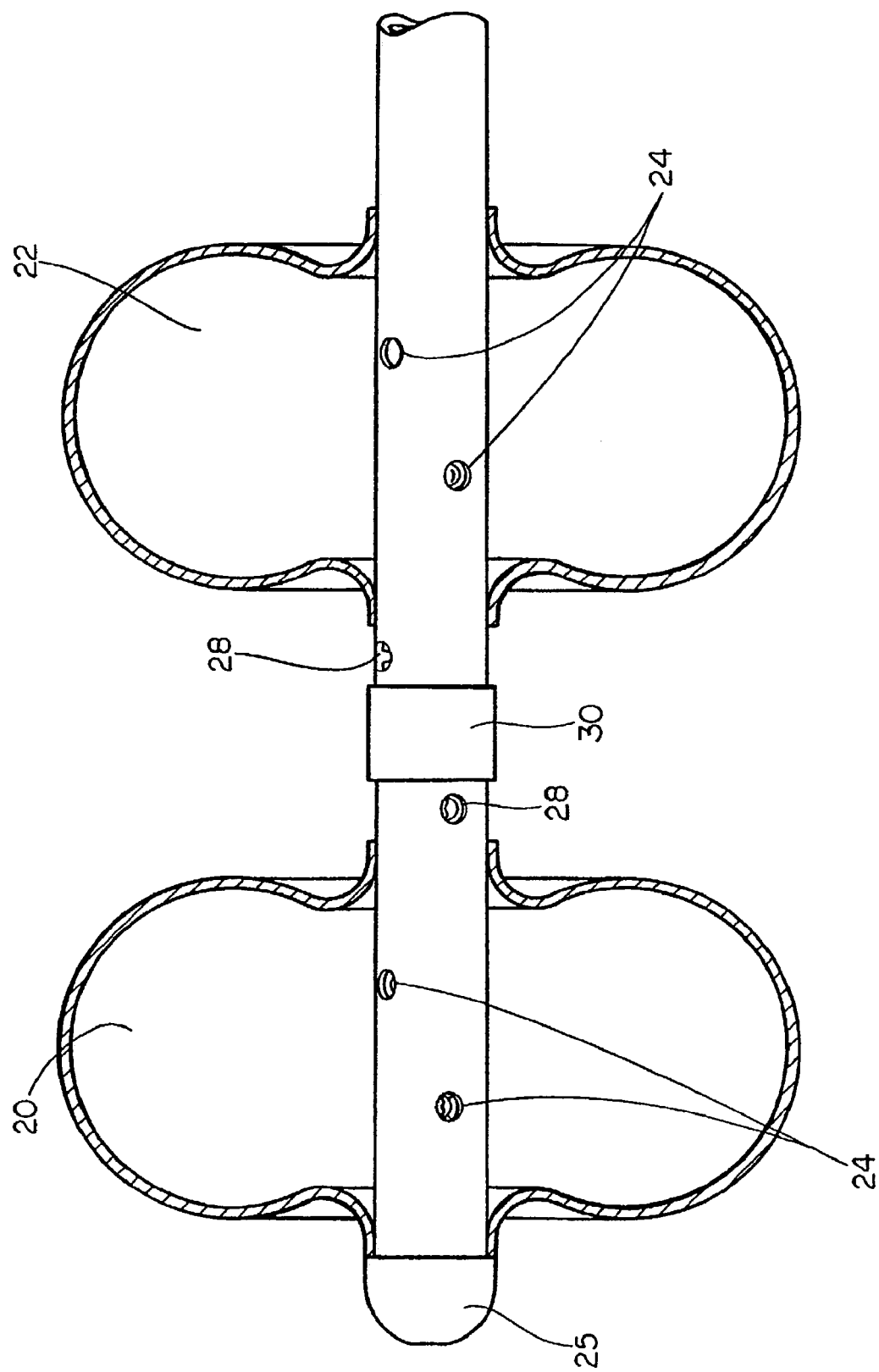
FIG. 7 is a side view of the distal portion of the ablation catheter of FIG. 3 with balloons inflated.

Associated with the balloons is one or more conventional lumens (not shown) located within the catheter for inflation of the balloons and one or more openings (24) in the catheter as shown in FIGS. 5, 6 and 7. Those openings (24) are located in the surface of the catheter (12) inside the balloon in communication with lumen to receive the media used to inflate and vent the balloons. Inflation of the balloon is accomplished using conventional methods, preferably a radiopaque contrast solution, and more preferably a marked saline solution. In addition, if desired, radiopaque marker bands may be secured to the balloons to mark their relative position. Preferably, a tip electrode (25) is secured to the catheter (12) at a position distal to the distal balloon (20). This tip electrode (25) is utilized to monitor the electrical activity within the pulmonary vein distal to the balloons (20, 22) and to discover or map the location within the pulmonary vein for the atrial premature contraction. Once that location is determined, the catheter (12) may be withdrawn slightly within the pulmonary vein from this location so that the subsequently formed circumferential ablation lesion will be located proximal from the source of the premature atrial contraction.

When the distal balloon (20) is inflated, it should completely prevent the flow of blood through the pulmonary vein (14) around the balloon. In order to assure that this distal balloon (20) forms a tight seal, a system to introduce a contrast media may be provided at a location distal to the distal balloon, such as a lumen in the catheter with an opening in the surface of the catheter (not shown). Contrast media may then be introduced into the vessel distal to the distal balloon (20) to identify if any leaks exist around the distal balloon (20). If such leaks do exist, additional pressure may be supplied to the balloon until distal balloon (20) completely stops the flow of blood into the space between the two seals.

Proximal from the first seal is the second seal. In one preferred embodiment, this second seal is a proximal balloon (22) of similar construction to the distal balloon (20). The purpose of proximal balloon (22) is to seal off any backflow of blood from the left atrium back into the pulmonary vein. While the structure of this proximal balloon (22) is similar to that of the distal balloon, it preferably has the capability to inflate to a greater diameter than that of the first balloon because it must be inflated at a location in the pulmonary vein closer to the os of the pulmonary vein than is the distal balloon (20) and, in fact, may be at the os itself. As pulmonary veins approach the left atrium, their diameters increase. While this proximal balloon (22) preferably must substantially occlude this larger diameter, it need not, and preferably will not, seal tightly against the walls of the pulmonary vein, as is necessary for the distal balloon (20). In a preferred embodiment, the seal created by the proximal balloon (22) need only prevent the backflow of blood into the space between the proximal and distal balloons. In fact, in a preferred embodiment, the seal created by the proximal balloon (22) must not be so tightly sealed against the walls of the pulmonary vein to prevent conductive media, which is introduced into the space between the proximal and distal balloons (20, 22), to escape around the edges of the proximal balloon (22). Because of the pressure created against the outside edges of the proximal balloon (22) by continuous introduction of conductive media into the space between the proximal and distal balloons (20, 22), the seal created by the proximal balloon (22) must be loose enough to permit excess conductive media to escape around the proximal balloon (22). This constant flow of conductive media away from the seal formed by the proximal balloon (22) guarantees that blood does not backflow into the space or area between the two balloons from the left atrium and also washes out any blood that may enter the space from around the seal formed by the distal balloon (20). Conventional inlet openings (24) are also located in the catheter (12) inside proximal balloon (22) to inflate proximal balloon (22).

Figure 10:
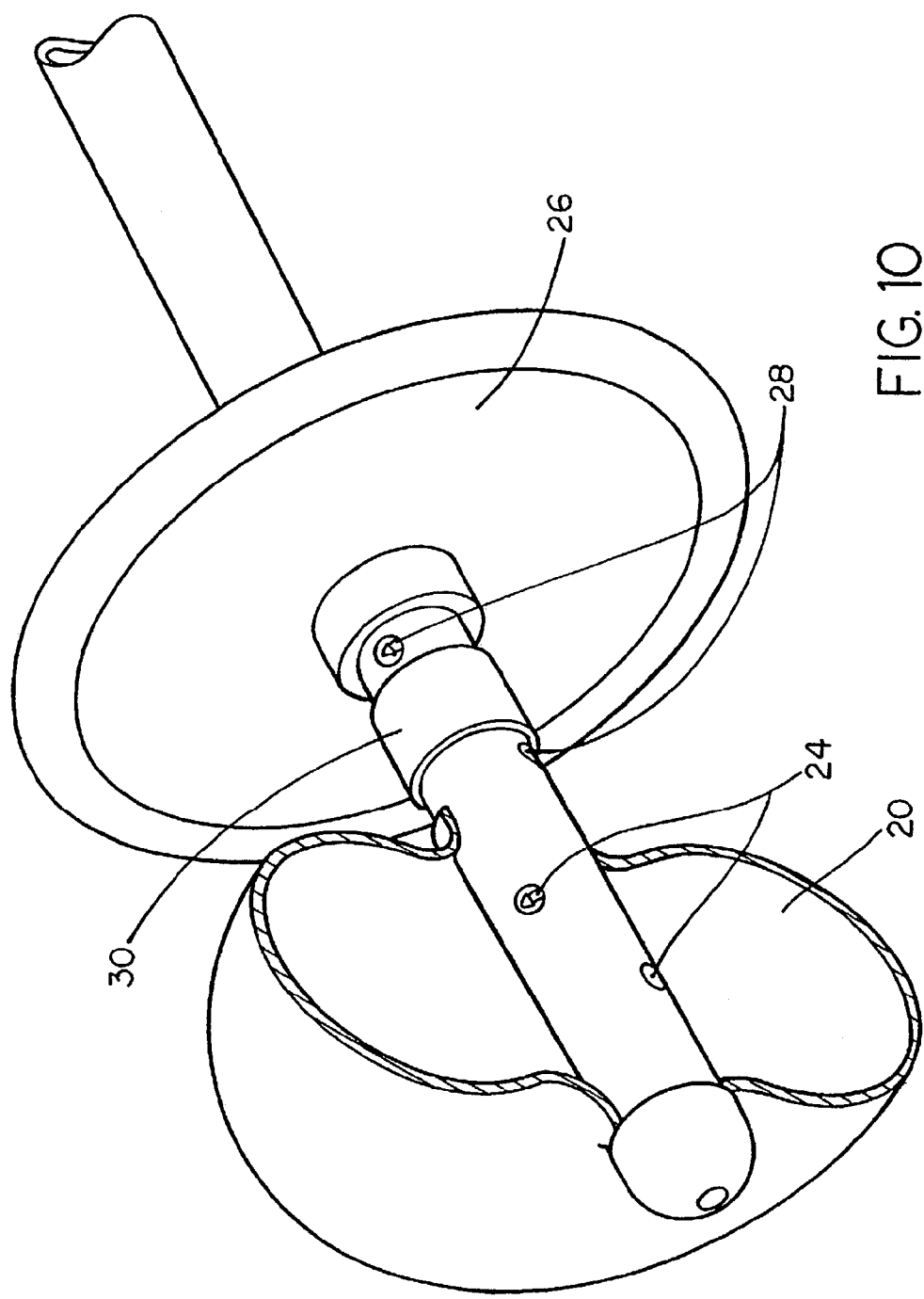
FIG. 10 is a perspective view of the distal portion of the ablation catheter of FIG. 8 with single balloon inflated.

In an alternative preferred embodiment, the second seal is a flexible disk (26) as shown in FIGS. 8, 9, and 10. This flexible disk (26) functions in a manner similar to that of the proximal balloon (22), i.e., it substantially seals the pulmonary vein to prevent the backflow of blood into the space between the distal balloon (20) and the disk (26).

The term "flexible" refers to the disk (26) folding on itself in a manner similar to that of an umbrella being closed when the device to which the disk (26) is secured is located within an introducer. Once the medical device to which the flexible disk is secured is extended from the tip of the introducer, the disk returns to its conventional disk-shape.

By constructing the diameter of the disk (26) of sufficient size, it will be effective in substantially sealing the pulmonary vein (14). As the flexible disk (26) is preferably only used as the second seal, it is not necessary that it completely seal off the pulmonary vein (14) as this would interrupt the flow of conductive media. In fact, as discussed above, it is important that there be sufficient space between the disk (26) and the wall of the pulmonary vein to permit blood and conductive media that is introduced between the distal balloon (20) and the disk (26) to escape around the outside surface of the disk (26) and to continually flush the space between the distal balloon (20) and the disk (26). Thus, the overall diameter of the disk when extended should be at least about 5 mm (0.2 in.) and preferably at least about 20 mm (0.8 in.). The thickness of the disk is not particularly critical as long as it is of sufficient strength to maintain the disk in its extended position and thus should have a thickness of at least about 1 millimeter (0.004 inch). The flexible disk (26) is preferably made of biocompatible material such as silicone.

Conductive media is introduced between the first and second seals through one or more conductive media openings (28) in the catheter located between the first and second seals, for example, as shown in FIGS. 4 and 9. Preferably two openings are provided between the two seals so that the flow of the conductive media will be uninterrupted during the ablation procedure. This media is introduced through a lumen (not shown) passing through the catheter then through the media openings (28) into the space between the seals with the flow of this conductive media monitored by conventional methods. By locating the media openings (28) between the two seals and by filling the space between the two seals with media, any blood present in the area between the two seals is flushed away.

In one embodiment, the conductive media is a saline solution marked with markers so that it can be monitored by fluoroscopy, although any appropriate conductive media may be used. The preferred source for the ablation energy is radio frequency energy. During an ablation process, the radio frequency energy from the ablation catheter is carried through the conductive media to the tissue. In a preferred embodiment, the impedance of the conductive media should be less than the impedance of the human tissue so that the tissue will heat up to an ablation temperature at a faster rate than does the media.

As stated above, in a preferred embodiment the second seal is not secured as tightly against the walls of the pulmonary vein as is the first seal. By this arrangement, as the conductive media is continually introduced into the space between the two seals, it will continually flush out any blood which seeps into the space between the two seals and replace that blood with conductive media.

In an alternative embodiment, a chemical ablating material is injected through the media openings (28) into the space between the first and second seals. The chemical ablating material ablates the tissue of the vessel located between the first and second seals. In this embodiment, in contrast with the earlier embodiments, the second seal must be a balloon. This proximal balloon must also be secured tightly against the surface of the vessel to seal the vessel. In contrast to the first preferred embodiment where the conductive media escapes around the edges of the second seal, when the chemical ablating material is used, this material should not escape from the space between the two seals around the edges of the second seal. Thus, in this embodiment the proximal balloon should fit tightly against the vessel to prevent not only the backflow of blood from the left atrium, but also the escape of the chemical ablating material from between the two balloons.

The chemical ablating material is introduced into the space between the two balloons (such as 20 and 22 as shown on FIG. 7) through a lumen and the media opening or openings (28) in the surface of the catheter (12) located between the two balloons. The types of chemical ablating materials that can be utilized for this ablation procedure include any liquid material which will ablate cardiac tissue and preferably includes any anhydrous alcohol. Once the chemical ablating material has successfully ablated the tissue, it should be flushed out by introducing a flushing media into the space between the two balloons. The flushed chemical ablating material and the flushing media are removed through one of the media openings (28) in the catheter into a lumen to be discarded.

In all embodiments it is important that the space between the first and second seals not be too large. If there is too much space between the two seals, it will be difficult to form an adequate circumferential lesion as the energy, preferably radio frequency energy, will be dispersed over too large a space. Thus, in a preferred embodiment, the distance between the distal balloon (20) and the proximal balloon (22) when inflated or disk (26) should be no more than about 10 mm (0.39 in.) and preferably from about 2 mm to about 4 mm (0.08 in. to about 0.16 in.). Notwithstanding, the distance between the two balloons or balloon and disk can be increased or decreased depending upon a number of conditions including but not limited to the thickness of the pulmonary vein, the diameter of the opening in the pulmonary vein at the point of ablation, the amount of energy being supplied by the ablating system, and the quantity of media needed to fill the space between the two seals.

Also secured to the catheter between the two seals is the ablating member or system. In a preferred embodiment as shown in FIGS. 3–7, the ablation system is a radio frequency ring electrode (30) secured to the catheter (12) operating in conjunction with the conductive media that has been introduced between the two seals. By choice of an appropriate conductive media, upon the introduction of energy to the space between the two seals, the energy will be transferred through the media to the surface of the tissue of the pulmonary vein located between the two seals. By continuing to introduce energy for a sufficient period of time as is determined by the physician, a circumferential lesion will be formed in the tissue. Other forms of energy can also be used for the ablation.

In order to monitor the formation of this lesion, a temperature sensor, such as thermistors or thermocouples (not shown) may be secured to the catheter. Sensing electrodes (not shown) can also be secured to the catheter between the two seals to monitor electrical activity in the pulmonary vein.

Figure 11:
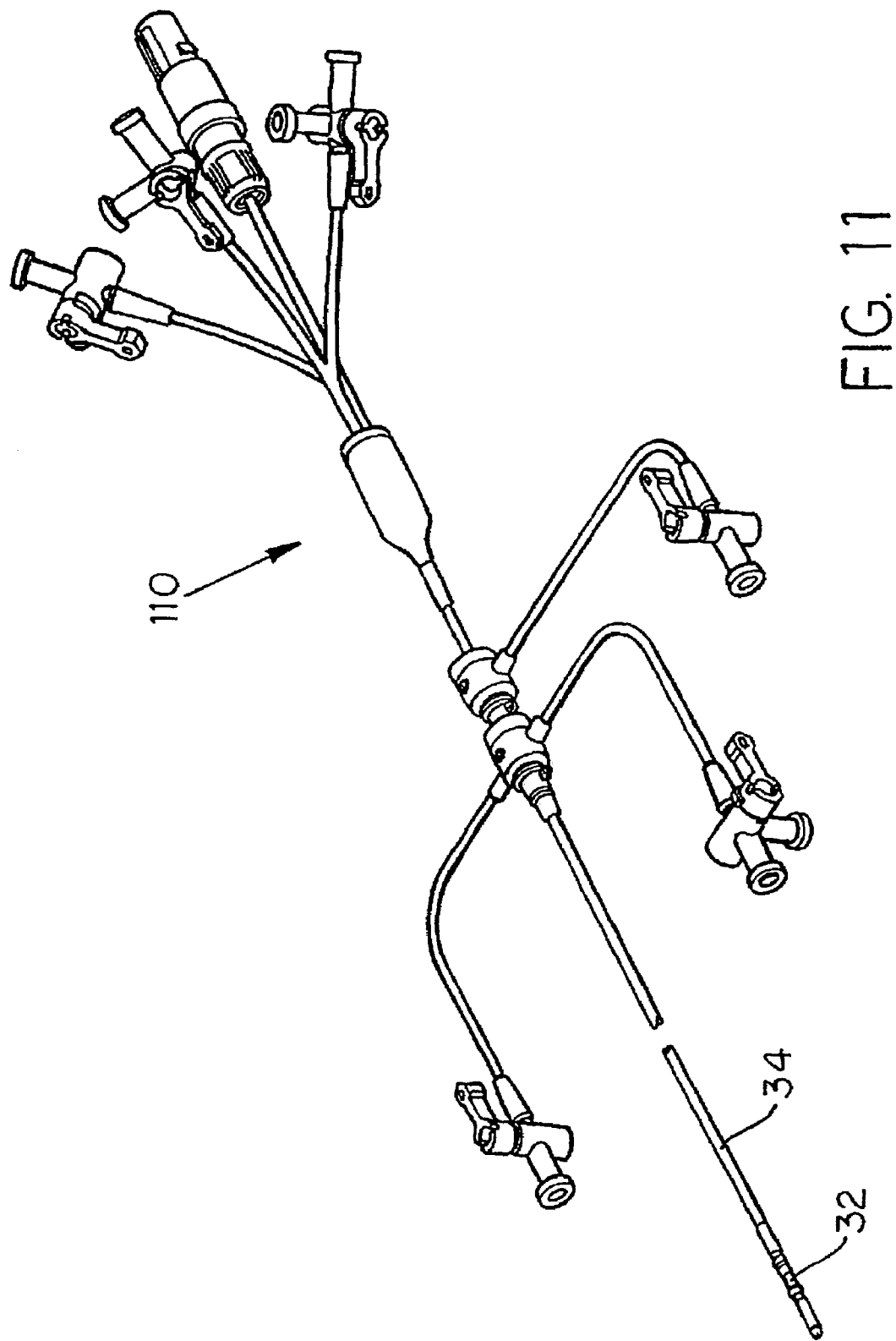
FIG. 11 is a perspective view of an alternative embodiment of the present invention comprising a medical system with an introducer and a catheter utilized in combination, with one balloon secured to the introducer and one balloon secured to the catheter, neither inflated.
Figure 13:
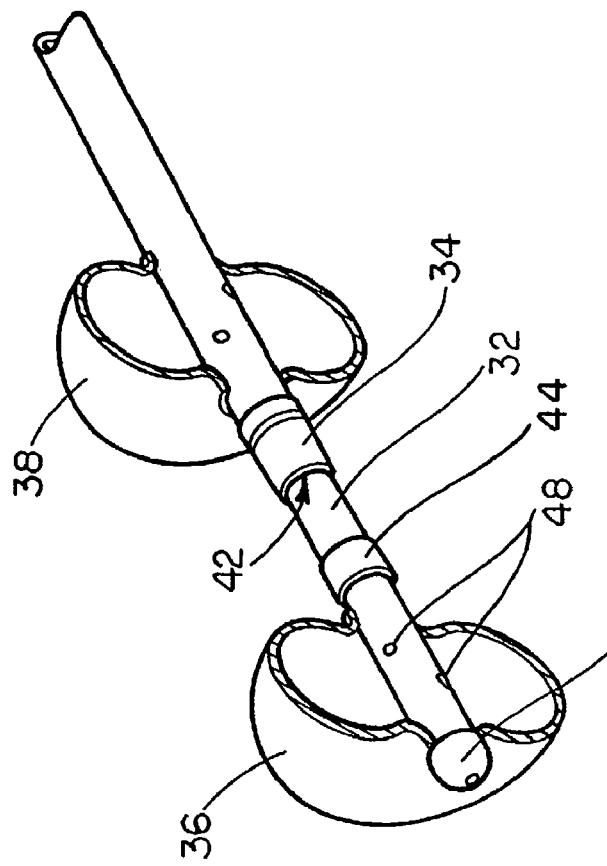
FIG. 13 is a perspective view of the distal portion of the medical system of FIG. 11 with two balloons inflated.
Figure 12:
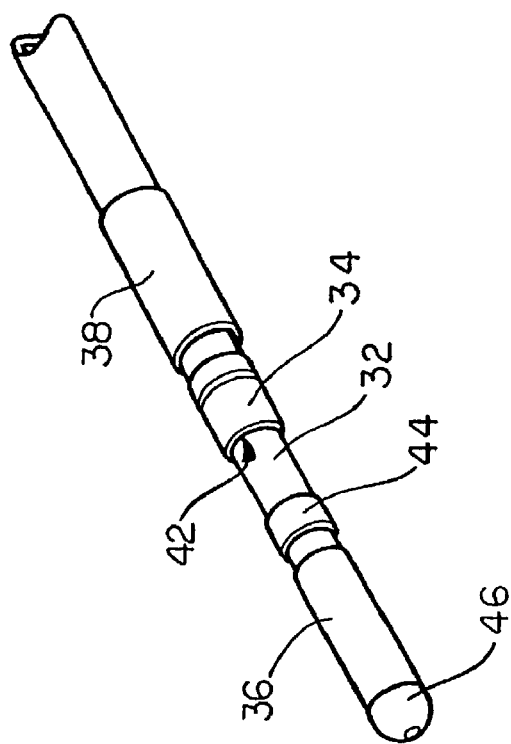
FIG. 12 is a perspective view of a distal portion of the medical system of FIG. 11 with two balloons not inflated.

In an alternate preferred embodiment, as shown in FIGS. 11–16, each of the first and second seals are secured separately to one of two medical devices, such as a catheter (32) and an introducer (34). The two medical devices form a medical device system (110). In this alternative preferred embodiment, the first seal or distal balloon (36) is secured to the catheter (32) in the manner discussed above, while the second seal is secured at or near the distal tip of the introducer (34) into which the catheter (32) is introduced. This second seal, which is secured to the introducer (34), is the same as the second seal above discussed and thus may be a proximal balloon (38) as shown in FIGS. 11–13 or a flexible disk (40) as shown in FIGS. 14 and 16. When using this embodiment, the first and second seals are utilized to form the space between them. However, because each of the seals is secured to separate medical instruments, the space between the two seals can be adjusted, as needed. By controlling the size of the space between the two seals, the physician can also control the size of the lesion formed during the ablation procedure. Because the diameter of the pulmonary veins may vary, resulting in greater or lesser volume of media being introduced between the seals, it may be appropriate to adjust the distance between the two seals. In a preferred embodiment, the distance between these two seals is at least about 0.5 mm (0.02 in.) and more preferably from about 2 mm (0.08 in.) to about 4 mm (0.16 in.).

In this embodiment, the other components of the system for production of a circumferential ablation lesion within a pulmonary vein can be secured to either the catheter (32) or introducer (34), as appropriate. For example, the conductive media may be introduced through a lumen and an injection port located either in the catheter or in the introducer or the media may pass through a lumen in the introducer exiting at the introducer's distal tip (42) as is shown, for example, in FIGS. 12 and 15, to flush out the blood located between the two seals.

In this embodiment, the tip electrode (46) is secured at or near the distal tip of the catheter (32) so that it can sense the presence of premature atrial contractions within the pulmonary vein.

The ablating system for this embodiment, preferably a ring electrode (44), may be secured to either the catheter (32) or the introducer (34). However, it is preferably secured to the catheter (32) at a location proximal from the distal balloon (36) as shown in FIGS. 11 and 14. Openings (48) leading to lumens (not shown) are also provided in the catheter (32) and the introducer (34) for introduction of media to inflate the balloons (36, 38). A temperature sensing mechanism (not shown) may also be secured to either the catheter (32) or the introducer (34) at an appropriate location.

This two-part system (110) utilizing an introducer (34) with a proximal balloon (38) and a catheter (32) with a distal balloon (36) may also be used with the chemical ablation system as long as both the proximal and distal balloons are securely sealed against the wall of the vessel. In all other ways this embodiment is similar to those previously discussed.

In operation, a modified Seldinger technique is normally used for the insertion of the medical device (10) into the body. Using this procedure, a small skin incision is made at the appropriate location to facilitate catheter or dilator passage. Subcutaneous tissue is then dissected, followed by a puncture of the vessel with an appropriate needle with a stylet positioned at a relatively shallow angle. The needle is then partially withdrawn and reinserted at a slightly different angle into the vessel making sure that the needle remains within the vessel. The soft flexible tip of an appropriate size guidewire is then inserted through, and a short distance beyond, the needle into the vessel. Firmly holding the guidewire in place, the needle is removed. The guidewire is then advanced into the right femoral vein and through the inferior vena cava into the right atrium. (The preferred procedure uses the inferior approach to the right and left atria. Procedures for the retrograde and superior approach to the left atrium can also be used.) With the guidewire in place, a dilator is then placed over the wire with the introducer to be used placed over the dilator. The dilator and introducer generally form an assembly to be advanced together along the guidewire into the inferior vena cava.

A Brockenbrough needle or trocar is then inserted through the lumen of the dilator to the right atrium to be used to create an opening through the interatrial septum, preferably at the fossa ovalis. The entire assembly (dilator and Brockenbrough needle) passes through the vena cava into the right atrium so that the tip rests against the interatrial septum at the level of the fossa ovalis. The Brockenbrough needle is then advanced within the dilator to reach the fossa ovalis. After an opening is made through the interatrial septum, the needle, dilator and first guiding introducer for the left atrium are advanced into the left atrium. After the introducer is advanced through the interatrial septum into the left atrium, the Brockenbrough needle and dilator are removed leaving the introducer in the left atrium. The ablation catheter (12) is then advanced through the lumen of the introducer and is placed within the left atrium. After the catheter (12) is advanced through the lumen of the introducer into the left atria, a precurved guiding introducer is advanced over the catheter to assist in the placement of the ablation catheter within the appropriate pulmonary vein as shown in FIG. 2.

Once the distal end (16) of the ablation catheter (12) has been advanced into the pulmonary vein (14), it is positioned within that pulmonary vein by use of a sensing tip electrode (25) secured at or near the distal end (16) of the catheter (12) as shown in FIGS. 3–7. This sensing tip electrode (25) senses electrical activity within the pulmonary vein, including atrial premature contractions. Once the source of the atrial premature contractions has been confirmed to be distal to the sensing tip electrode (25), the distal balloon (20) is inflated using conventional procedures. This distal balloon (20) must be sufficiently inflated to prevent completely the flow of blood through the pulmonary vein (14) around this balloon (20). To assure that no blood flows around this balloon, marked media may be injected into the pulmonary vein (14) at a point distal from the distal balloon (20) through a lumen in the catheter. Any leakage around the distal balloon (20) can then be determined by fluoroscopy and eliminated by additional pressure on the distal balloon (20). Once the distal balloon (20) is properly inflated in the pulmonary vein, a proximal balloon (22) is inflated. The second, proximal balloon (22) need only substantially prevent the backflow of blood into the pulmonary vein (14) from the left atrium. In order to assure that the proximal balloon (22) is properly but not overly inflated, conductive media is introduced into the space between the distal (20) and proximal (22) balloons through conventional conductive media openings (28) located in the catheter (12) between the two balloons (20, 22). This conductive media flushes out any blood located between the two balloons around the edge of the proximal balloon (22). A continual flow of conductive media into this space between the balloons throughout the procedure prevents any backflow of blood from the left atrium and provides a source of constant cooling while ablation energy is being applied. The ablating system, preferably an RF ring electrode (30), is secured to the catheter (12) between the two balloons (20, 22). The RF electrode (30) emits energy which is conducted by the conductive media to the tissue in the vein between the balloons. Sufficient energy is emitted to create a circumferential lesion of sufficient width and breadth to block the passage of atrial premature contractions. The temperature of the tissue may be monitored by temperature sensors, such as thermistors or thermocouples (not shown), located on the surface of the catheter (12) between the two balloons (20, 22). In addition, sensing electrodes (not shown) may be located between the two balloons or proximal from the balloon to sense electrical activity through the vessel after the ablation procedure has been completed to assure complete blockage of the pulmonary vein.

In an alternate preferred embodiment, as shown in FIGS. 8, 9 and 10, the proximal balloon (22) can be replaced by a flexible disk (26) which will perform in generally the same manner as the proximal balloon (22) described above.

In an alternate preferred embodiment, the catheter (12) with two balloons (20, 22) is replaced by a catheter (32) containing the distal balloon (36) and an introducer (34) containing the proximal balloon (38). All other components of the system are similar to those of the first preferred embodiment. In all other aspects, this alternative preferred embodiment performs the ablation procedure in the same way as above discussed for the first preferred embodiment. The proximal balloon (38) of this embodiment secured to the introducer (34) may also be replaced with a flexible disk (40) as shown in FIGS. 14–16.

After the ablation procedure has been completed and tested by use of sensing electrodes, each of the elements of the system are removed from the pulmonary vein and left atrium. If desired, additional sensing devices can be introduced into the left atrium to determine whether there are any other sources for the atrial premature contractions in other pulmonary veins.

It will be apparent from the foregoing that while particular forms of the invention have been illustrated and described, various modifications can be made without departing from the spirit and scope of the invention. For example, the present invention could also be used for ablation procedures in other vessels such as the coronary sinus and other veins.

We claim:

1. A medical device for ablation within an animal vessel, the medical device comprising:
    (a) a catheter having a distal end for insertion into the animal vessel and a proximal end that remains outside the animal vessel;
    (b) a first inflatable seal secured to said catheter at a first location, said first inflatable seal being adapted to seal the animal vessel to prevent a flow of blood through the animal vessel;
    (c) a second seal secured to said catheter at a second location, said second location being between said first location and said proximal end of said catheter, said second seal being adapted to limit a backflow of blood into the animal vessel, wherein the second seal is a flexible disk;
    (d) at least a first opening in said catheter adapted to introduce a first inflating fluid to inflate said first inflatable seal; and
    (e) an introduction member secured to said catheter to introduce a fluid media into the animal vessel at a location between said first inflatable seal and said second seal, wherein the fluid media is adapted to ablate tissue comprising at least part of the animal vessel between said first inflatable seal and said second seal.

2. The medical device of claim 1, wherein said first inflatable seal is an inflatable balloon.

3. The medical device of claim 1, wherein said introduction member comprises a lumen passing through the catheter to an opening in the catheter between the first and second seals.

4. The medical device of claim 1 further comprising a sensor for sensing cardiac activity, wherein the sensor is secured to the catheter.

5. The medical device of claim 1, wherein the fluid media is a conductive fluid media.

6. The medical device of claim 5, wherein the conductive fluid media has an impedance that is less than the impedance of the tissue.

7. The medical device of claim 1, whereby during the ablation procedure, the second seal is structured to encourage a flow of the fluid media around the second seal away from the location between the first and second seals when the fluid media is introduced into that location.

8. The medical device of claim 1, wherein the second seal has a maximum sealing diameter that is greater than a maximum sealing diameter of the first seal.

9. The medical device of claim 1, wherein the at least part of the animal vessel is a circumferential surface defined substantially by the first and second seals.

10. The medical device of claim 1, wherein the catheter further includes a generally continuous outer circumferential surface and the first and second seals are secured to the surface.

11. The medical device of claim 10, wherein the opening is in the outer circumferential surface.

12. The medical device of claim 1 further comprising an electrode located between the first inflatable seal and the second inflatable seal.

13. The medical device of claim 12 wherein the fluid media is a conductive media that receives energy from the electrode and is thereby adapted to ablate tissue comprising at least part of the animal vessel between the first and second seals.

* * * * *